United States Patent [19]
Reid

[11] Patent Number: 5,859,359
[45] Date of Patent: Jan. 12, 1999

[54] CURLING STONE COMPARATOR

[75] Inventor: J. Gavin Reid, Kingston, Canada

[73] Assignee: Queen's University at Kingston, Kingston, Canada

[21] Appl. No.: 806,246

[22] Filed: Feb. 21, 1997

[51] Int. Cl.$^6$ .................................................. G01N 33/00
[52] U.S. Cl. ...................... 73/12.05; 73/12.09; 73/865.9; 124/61; 273/129 AP
[58] Field of Search .................. 73/12.05, 12.11, 73/12.09, 865.9; 124/61, 73; 273/129 AP, 129 S, 129 V, 128 CS, 128 A, 108.1

[56] References Cited

U.S. PATENT DOCUMENTS

| | | | |
|---|---|---|---|
| 3,507,264 | 4/1970 | Whitmore et al. | 124/61 |
| 3,608,211 | 9/1971 | Carr | 273/129 R |
| 3,665,910 | 5/1972 | Boni | 273/129 S |
| 3,777,548 | 12/1973 | Nicolaides | 73/12.11 |
| 3,793,874 | 2/1974 | Shockey et al. | 73/12.11 |
| 4,086,902 | 5/1978 | Reynolds | 124/61 |
| 4,557,483 | 12/1985 | Kimura | 273/129 S |
| 5,337,726 | 8/1994 | Wood | 124/61 |
| 5,535,627 | 7/1996 | Swanson et al. | 73/12.11 |
| 5,647,338 | 7/1997 | Martin | 124/73 |

FOREIGN PATENT DOCUMENTS

| | | | |
|---|---|---|---|
| 161363 | 11/1985 | European Pat. Off. | 124/61 |

*Primary Examiner*—Hezron Williams
*Assistant Examiner*—Nashmiya Fayyaz
*Attorney, Agent, or Firm*—Richard J. Hicks

[57] ABSTRACT

A simple pneumatic device for use in comparing and matching curling stones, and evaluating ice surfaces and sweeping broom efficiencies is described. A pneumatic cylinder, charged by means of a compressed gas, is placed against the backboard of a rink and operated to propel a curling stone with a predetermined and accurately controlled force along a sheet of curling ice.

5 Claims, 2 Drawing Sheets

CURLING STONE COMPARATOR

FIELD OF INVENTION

This invention relates to a method and device for comparing and matching curling stones and the like. More particularly, this invention relates to a machine for propelling curling stones along an ice surface with a predetermined force for comparison purposes or to evaluate the quality of the ice surface or to assess the effect of sweeping.

BACKGROUND OF INVENTION

Comparing and matching curling stones and comparing sweeping brooms and the effects of brushing are important factors in the sport of curling. The quality of the ice surface is also important. Heretofore, however, efforts to make meaningful comparisons have been hampered because there is no known method or apparatus for ensuring that each stone is propelled down the ice with exactly the same force. At best, human throwers attempt to propel each stone using as consistent a throwing force as possible. Such an approach is clearly suspect and does not provide sufficient accuracy for comparative research purposes. Attempts have also been made to launch curling stones down sloping ramps or to hit a stone with the ball of a pendulum, but these attempts are not entirely satisfactory or accurate enough for research purposes.

Mechanical launching devices for propelling bowling balls, marbles, hockey pucks and the like are, of course, well known and generally rely on spring-loaded guns or are cable transmitted pusher devices such as that shown in U.S. Pat. No. 3,608,211, issued 28 Sep. 1971, for a launching device for demonstrating collision principles. A curling stone, however, weighs approximately forty-four pounds and spring-loaded guns capable of handling such a load are extremely cumbersome and difficult to load manually. There is a need, therefore, for a simple propelling device for curling stones and the like which applies a consistent propelling force every time it is used so as to provide a consistent "stone throw" which can be used to compare any of: individual stones, ice surfaces, efficiency of sweeping, broom design and other variables in the sport of curling.

OBJECT OF INVENTION

It is an object of the present invention to provide a pneumatic device for propelling curling stones or the like with a consistently applied projecting force. Another object is to provide a method for comparing curling stones, brooms and sweeping techniques and to assess the quality of ice in a curling rink.

BRIEF STATEMENT OF INVENTION

By one aspect of the present invention, there is provided a device for propelling an object forward along a surface at a preselected initial velocity, comprising: cylinder means including a piston moveable between a retracted position and an extended position; means mounted on said piston to releasably engage said object; fluid flow path means between a source of compressed gas and said cylinder means; gas pressure regulating means in said fluid flow path; and shut off valve means in said fluid flow path intermediate said gas pressure regulating means and said cylinder means, whereby said compressed gas, at a selected pressure, can be introduced into said cylinder and thereby move said piston from retracted position to said extended position and thus imparting a selected propelling force to said object.

By another aspect of the present invention, there is provided a method for comparing curling stones comprising:
(a) mounting a pneumatic cylinder means, including a piston moveable between a retracted position and an extended position, on an ice surface and in contact with a backstop thereon, with said piston in said retracted position;
(b) placing a selected said curling stone in releasable contact with said piston;
(c) activating said cylinder means with a preselected gas pressure so as to move said piston to said extended position and thereby propel said stone over said ice surface with a preselected initial velocity; and
(d) measuring the distance travelled by said stone over said ice surface.

DETAILED DESCRIPTION OF PREFERRED EMBODIMENTS

As used herein, the term "pneumatic" means acting by means of air or other gas.

Figure 1:
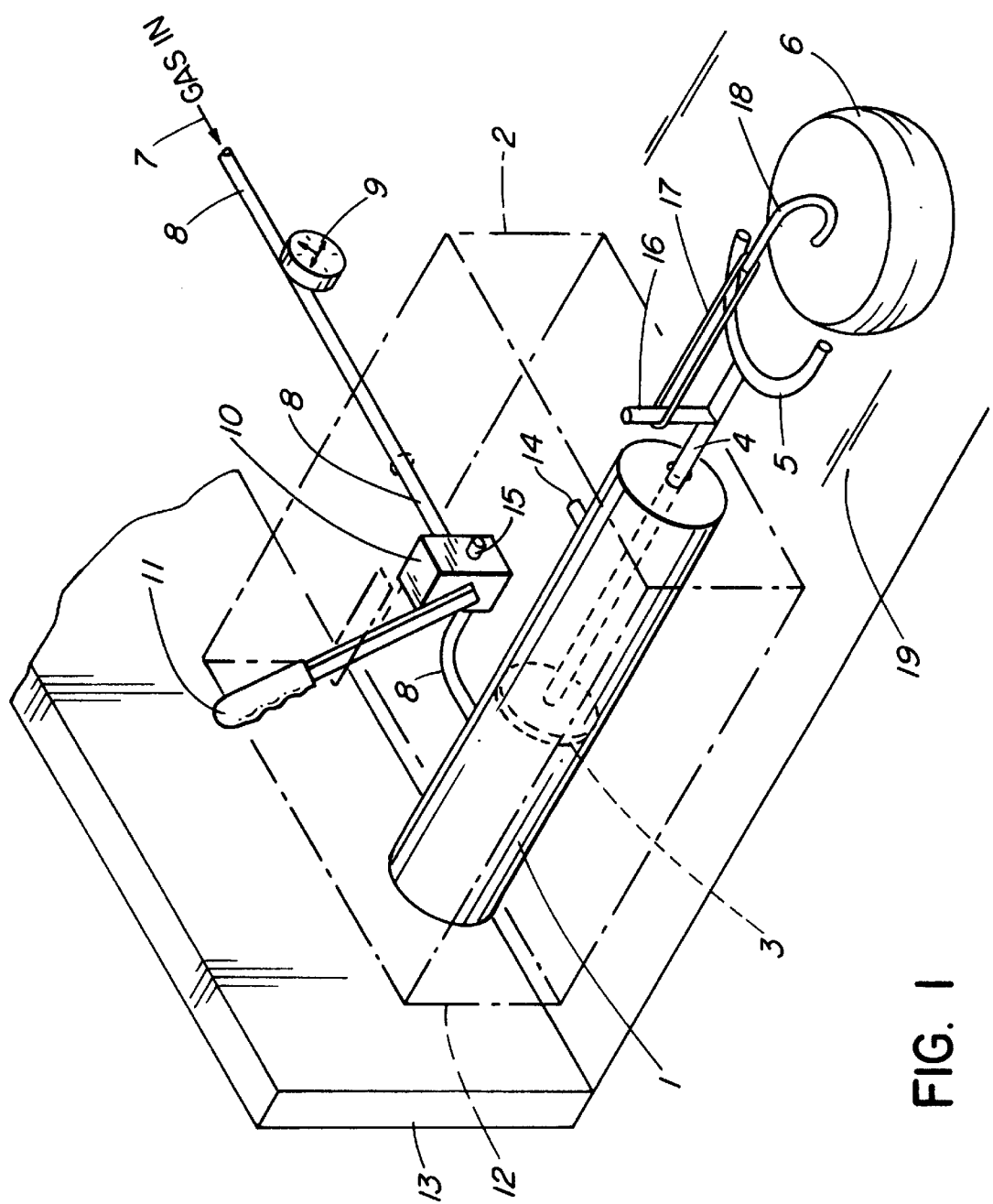
FIG. 1 is a schematic isometric view of an apparatus according to one embodiment of the present invention.

As seen in FIG. 1, a pneumatic cylinder is mounted horizontally in an outer casing or housing 2. A piston 3 is provided in cylinder 1, having an end 4 projecting outwardly from casing 2 and terminating in a V-shaped fitting 5 adapted to engage a curling stone 6. Preferably, but not essentially, pneumatic cylinder 1 is a double wall cylinder which is capable of developing 200 psi gauge, such as BIMBA Model #DWC1743-2.

An air/gas supply 7 is connected to a pressure hose 8 and pressure regulator 9 so as to provide a fluid flow path from the gas supply 7 to pneumatic cylinder 1. A shut-off valve 10 is also provided in the hose 8 to open and close the fluid flow path by means of a lever 11 mounted on the top of box 2.

In operation the box 2 is placed on a sheet 19 of curling ice with the end 12 against the backboard 13 of the rink, and connected to gas supply 7. Any desired pressure is selected on regulator 9. Piston 3 is manually pushed rearwardly into cylinder 1 until fitting 5 is adjacent to the end thereof. Valve 10 is then opened by throwing switch 11 thereby allowing the compressed gas to enter cylinder 1 and pushing piston 3 forward and thus propelling stone 6 down the ice 19 with a preselected initial velocity. A pressure relief valve 14 allows air forward of piston 3 to escape to the atmosphere.

After each operation, piston 3 can be pushed back into the cylinder when a second pressure relief valve 15 is opened and valve 10 operated again to repeat the operation. It will be appreciated that the initial velocity of the stone 6 can be controlled by adjusting the pressure by means of regulator 9. Thus, a plurality of curling stones 6 can be compared and matched, the design and effectiveness of curling brooms can be evaluated, sweeping techniques can be evaluated and even the quality of the ice in the sheet 19 can be measured far more accurately than was heretofore possible.

Figure 2:
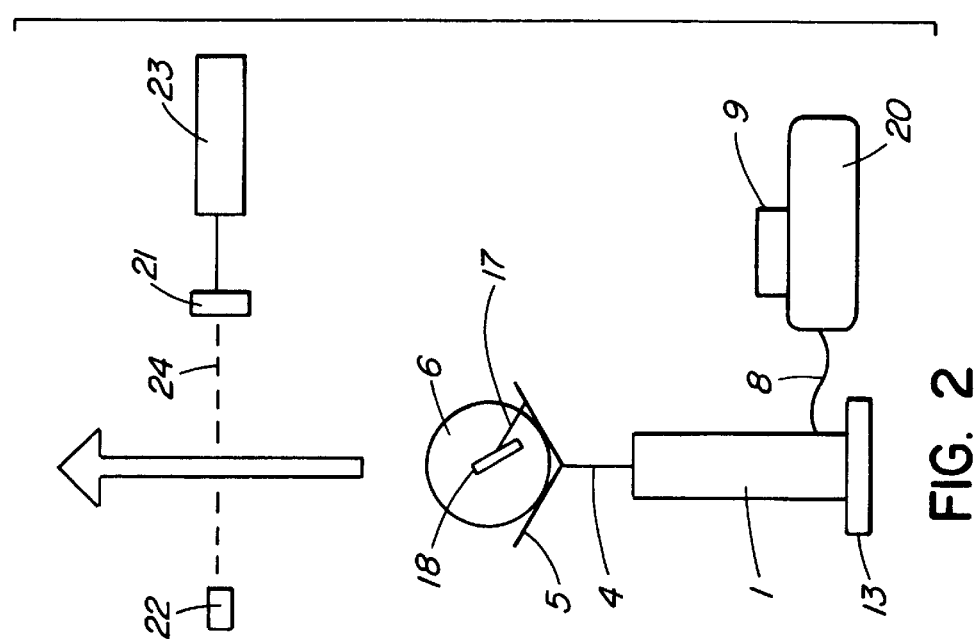
FIG. 2 is a schematic plan view of the embodiment of FIG. 1 in use for testing stones.

In a preferred embodiment a small mast 16 is mounted on rod 4 and an elastic band 17 is releasably connected to the handle 18 of stone 6. As soon as stone 6 moves forwardly and away from fitting 5 the band 17 releases but causes stone 6 to rotate slightly, thereby imparting the desired spin or rotation to stone 6 as it slides down the ice. The source of the compressed air is a matter of choice and may be directly from a central compressed air line, if readily available, or from an air tank or from a compressor. Most curling rinks do not have central compressed air and in order to make the device of the present invention as versatile as possible it may be preferable to provide a portable electric air compressor and tank 20, as shown in FIG. 2, which can simply be energized from any convenient power source.

EXAMPLE 1

To assess the reliability of the design, a single stone was launched ten times toward the house and the total distance travelled by the stone on each occasion was recorded. The resting position was recorded of each stone, and then each resting position was ranked in order from least distance to greatest distance travelled. The stones were then compared to the average distance to obtain an average deviation. All ten trials came to reset within the house and the average deviation was calculated to be 1.9% which shows an extremely high degree of consistency. A summary of these results is shown in table 1.

TABLE 1

Summary of results of stones launched consecutively towards the house.

| Trial | Distance Travelled | Distance from Meridian | Square of Distance from Meridian |
|---|---|---|---|
| 1 | 145 | 0 | 0 |
| 2 | 146.5 | +1.5 | 2.25 |
| 3 | 149.2 | +4.2 | 17.64 |
| 4 | 145 | 0 | 0 |
| 5 | 148 | +3 | 9 |
| 6 | 145 | 0 | 0 |
| 7 | 143.3 | −1.7 | 2.89 |
| 8 | 139.3 | −5.7 | 32.49 |
| 9 | 141.9 | −3.1 | 9.61 |
| 10 | 142.8 | −2.2 | 4.84 |
| Total | | | 69.72 |
| % Diff | | | 1.9% |

EXAMPLE 2

To establish the consistency of the device to propel a stone repeatedly with the same initial velocity, the device is set up against backboard 13 of an ice surface 19 and the same stone 6 was launched twenty times down the ice past an infra-red light source 21, reflector 22 and timer 23 as shown in FIG. 2. The time that the stone blocked the light beam 24 was recorded by timer 23. The results are shown in Table 2.

TABLE 2

Test for consistency of launcher by measuring initial velocity of stones.

| Trial | Time (sec) | Trial | Time (sec) |
|---|---|---|---|
| 1 | 0.079 | 11 | 0.079 |
| 2 | 0.070 | 12 | 0.070 |
| 3 | 0.071 | 13 | 0.069 |
| 4 | 0.081 | 14 | 0.071 |
| 5 | 0.080 | 15 | 0.074 |
| 6 | 0.080 | 16 | 0.072 |
| 7 | 0.079 | 17 | 0.072 |
| 8 | 0.079 | 18 | 0.078 |
| 9 | 0.079 | 19 | 0.079 |

TABLE 2-continued

Test for consistency of launcher by measuring initial velocity of stones.

| Trial | Time (sec) | Trial | Time (sec) |
|---|---|---|---|
| 10 | 0.076 | 20 | 0.081 |
| Mean ± SD | | | 0.0759 ± 0.004 |

To derive the velocity the diameter of the stone 6 was divided by the time, yielding an average initial velocity of 4 m/s. Since the times in table 2 are almost identical (SD±0.004), it may be concluded that the device is capable of launching stones 6 with a consistent initial velocity.

Sweeping plays an important role in the sport of curling. Brushes for brushing and brooms for sweeping are used to clean the ice in front of the moving stone to ensure that the desired trajectory is maintained and to guarantee that the stone travels as close to the required distance as possible. The use of brushing was believed by some to increase the likelihood of the stone coming to rest in the desired location.

Some theories proposed in the past as to why this was so are (1) the vacuum theory; (2) the burnish theory; and (3) the water film theory. The vacuum theory is based on the assumption that air in motion exerts less pressure on an object than air at rest. By sweeping, the air is put into motion and as a result less pressure is exerted on the stone, thus the stone may travel a greater distance. Although supported by several prominent curlers, this assumption has been shown to be incorrect. The burnish theory is based on the assumption that with an increase in the number of times the broom hits the ice, the ice would become polished and thus a decrease in surface tension would ensue. No empirical validation of this theory has ever been performed. The third theory, the water film theory, is based on the premise that as the ice is swept or brushed, friction causes the ice to melt for a brief period of time. Although none of the research conducted in the past on this subject was specific to curling, there is considerable scientific evidence to support this theory. The brushing produces a minute amount of heat due to friction, which is enough to melt the ice and lower the coefficient of friction for a brief period. This lowering of the coefficient of friction of the ice by sweeping or brushing, when combined with the residual melting of the ice due to friction by the action of the stone (granite) gliding over the ice, supports the water film theory.

EXAMPLE 3

A study was conducted to assess the effect of brushing with different brushes on the absolute distance travelled by a stone when the stone was launched reliably. Three tests were conducted, each on a different ice condition using the device of FIG. 1. The first was on ice that was neither fast nor slow (medium). The hog to T-line time being 23 seconds. Ice condition for the second test was slow (22 seconds) and the third was fast (24 seconds). Very slow or very fast ice conditions were not tested. Three brushes were tested during the first part, which took place on medium ice. The brushes tested were a Hammer brush, a Hog's Hair brush and a Brownie brush. In the second and third parts, the Hog's Hair brush was replaced with a Performance brush.

Figure 3:
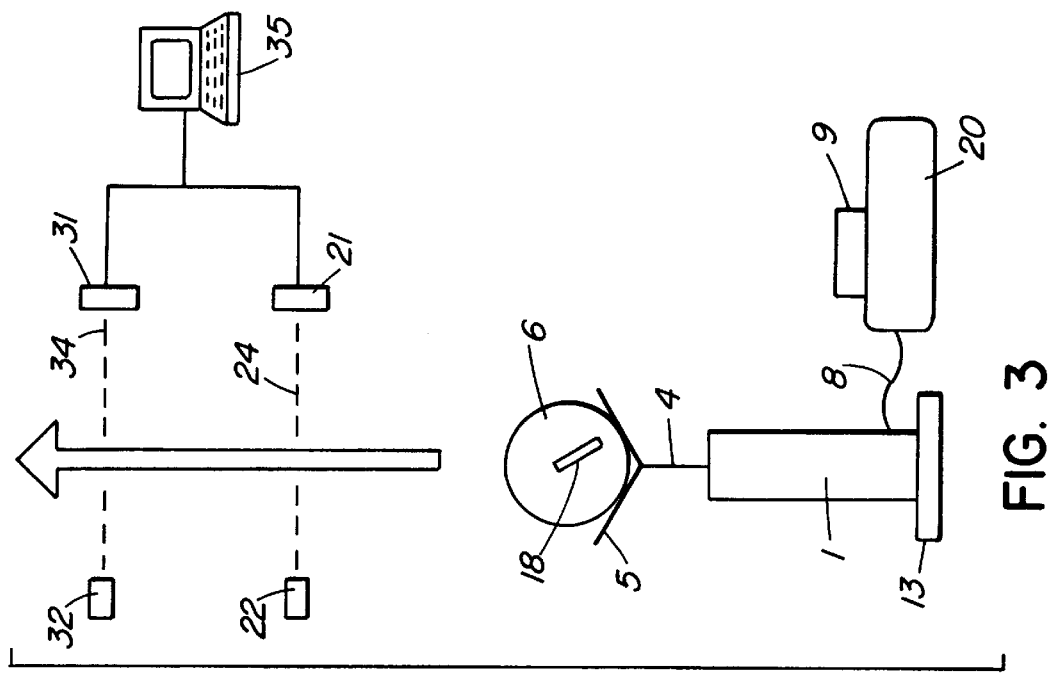
FIG. 3 is a schematic plan view of the embodiment of FIG. 1, in use for testing brushing efficiency.

The initial velocity of the stone recorded using two infrared lights, 21, 31, separated a distance of 1 metre, and a microcomputer 35 as shown in FIG. 3. The time the curling stone broke the path of the first infrared light 24 and the first reflector 22 was subtracted from the time the stone broke the path of the second infrared light 34 and the second reflector 32, when combined with distance $$\left(\text{avg. time} = \frac{dist}{\text{time}}\right),$$

the initial velocity could be calculated.

Since brushing technique varies from novice to expert, and expert brushers can be assumed to brush consistently, four experienced strong brushers were recruited for this experiment. From the hog line onward, two curlers were instructed to brush as hard as possible for all trials. The order in which the brushes were tested was randomized to alleviate any systematic bias.

RESULTS

Table 3 represents the outcome of three separate trials, respectively. Table 1 includes the coefficient of variation $$CV = 100\% \times \frac{SD}{\bar{x}}$$

(Rosner, 1990) for each trial. The CV expresses the variability of both the velocity as well as the distance the curling stone travelled between trials within each session. The average number of rotations of the stone was 2±½. The distances depicted are the distance the curlers brushed the stones, that is, from the hog line until the stone stopped. All stones travelled within 0.61 m of the centre line.

due to the different initial velocities, this is not viewed as a problem. Curlers will face varying ice conditions at different rinks as well as on different days; thus a more appropriate approach is to examine the trends within each trial. The different types of brushes seemed to have little effect on the distance travelled by the stones. Under "neither fast nor slow" ice conditions (23 seconds from hog to T-line), the Hammer brush produced the absolute greatest average distance over five trials, followed closely by the Brownie and the Hog's Hair. The range of values between the brushes was no more than 0.5 m. The control variable (no brushing) produced an average distance of about 1 m less than the Hog's Hair. Thus the brushes did produce an average increase in distance of about 1.1 m over the control, but no significant differences are observed between the brushes. An interesting attribute of the data is the consistency of the coefficient of variation under this condition. The velocity was very consistent, varying by no more that 2.6%, the distance travelled varied by between 2.6% and 4.1%, with the 2.6% being that of the control trial without brushing.

Under "slow" ice condition (22 seconds from hog to T-line) similar results were observed, even with velocity held constant. The Performance brush produced the overall greatest distance, followed closely by the Brownie, with the Hammer lagging about 0.8 m behind. The control variable (no brushing) produced slightly lower values. The total range between all three brushes and the control was not more than 1 m. The coefficients of variation for the distance travelled for this trial were slightly higher than those observed under neither fast nor slow ice conditions. Perhaps this is due to the varying ice conditions combined with an increase in initial velocity.

TABLE 3

Summary of results. The pressure of the air-compressor was set at 4.137 × $10^5$ Pascals (60 psi) for the neither fast nor slow ice condition, and 5.516 × $10^5$ (80 psi) Pascals for the fast and slow ice respectively.

| | Neither Fast nor Slow Ice | | | | | | | |
|---|---|---|---|---|---|---|---|---|
| | No Brushing | | Hammer Brush | | Hog's Hair Brush | | Brownie Brush | |
| | Vel(m/s) | Dist (m) | Vel(m/s) | Dist (m) | Vel(m/s) | Dist (m) | Vel(m/s) | Dist (m) |
| Mean | 1.836 | 13.51 | 1.861 | 14.852 | 1.836 | 14.36 | 1.832 | 14.696 |
| SD | 0.037 | 0.609 | 0.032 | 0.994 | 0.037 | 1.003 | 0.031 | 0.974 |
| CV | 2.0% | 2.6% | 1.7% | 4.0% | 2.0% | 4.1% | 1.7% | 4.0% |

| | Slow Ice | | | | | | | |
|---|---|---|---|---|---|---|---|---|
| | No Brushing | | Hammer Brush | | Performance Brush | | Brownie Brush | |
| | Vel(m/s) | Dist (m) | Vel(m/s) | Dist (m) | Vel(m/s) | Dist (m) | Vel(m/s) | Dist (m) |
| Mean | 2.388 | 22.154 | 2.388 | 22.378 | 2.388 | 23.168 | 2.3882 | 23.098 |
| SD | 0* | 2.416 | 0 | 2.490 | 0 | 2.001 | 0 | 1.873 |
| CV | N/A | 2.5% | N/A | 7.7% | N/A | 5.6% | N/A | 6.0% |

| | Fast Ice | | | | | | | |
|---|---|---|---|---|---|---|---|---|
| | No Brushing | | Hammer Brush | | Performance Brush | | Brownie Brush | |
| | Vel(m/s) | Dist (m) | Vel(m/s) | Dist (m) | Vel(m/s) | Dist (m) | Vel(m/s) | Dist (m) |
| Mean | 2.509 | 23.328 | 2.487 | 25.89 | 2.5102 | 24.762 | 2.5302 | 26.908 |
| SD | 0.088 | 5.827 | 0 | 1.715 | 0.087 | 4.169 | 0.059 | 2.774 |
| CV | 3.5% | 24.9% | 0 | 6.6% | 3.5% | 16.8% | 2.3% | 10.3% |

*The standard deviation of the data was 0 since initial velocity was constant.

Although comparison is difficult among the "neither fast nor slow" ice condition and the remaining two conditions, Under "slow" ice conditions the distance travelled by the stones increased as the trial progressed, since the trials were randomized, this had no effect on the assessment of the effectiveness of the brushes, but does provide insight into the behaviour of the ice as a game continues. Perhaps the texture and relative amount of pebbles in the ice changes as the games progress due to the cumulative effect of repetitive brushing and stones travelling over it. This factor would account for the increased coefficients of variation ranging between 5.6% and 7.7% under this condition. This effect is exemplified under fast ice conditions (24 seconds from hog to T-line) where large standard deviations of the distances travelled by the stones while being brushed by the brooms were observed.

As expected, under fast ice conditions the overall distance travelled by the stone increased by approximately 1 m over that observed under slow ice conditions. Under this condition, the range between brushes was 2.1 m, with the Brownie brush leading the Hammer and Performance respectively. On average, the brushing causes an increase in distance travelled by the stone of 2.5 m over the control variable of no brushing. The coefficients of variation for this trial, as depicted in table 3, are somewhat greater under this condition when compared to the previous two conditions.

I claim:

1. A devices connectable to a source of compressed gas, for propelling a curling stone forward along a horizontal ice surface at a preselected initial velocity, comprising: cylinder means, including a piston which is moveable between a retracted position and an extended positions for placement on said ice surface; means mounted on said piston to releasably engage said curling stone when said curling stone is in contact with said ice surface; fluid flow path means between said source of compressed gas and said cylinder means; gas pressure regulating means in said fluid flow path; and shut off valve means in said fluid flow path intermediate said gas pressure regulating means and said cylinder means, whereby gas, at a selected pressure, can be introduced into said cylinder means and thereby move said piston from said retracted position to said extended position, thus imparting a selected propelling force to said curling stone along said ice surface.

2. A device as claimed in claim 1 wherein said gas is air.

3. A device as claimed in claim 1 including means to impart spin to said curling stone.

4. A device as claimed in claim 1 including said source of compressed gas connected in fluid communication to said fluid flow path means.

5. A device as claimed in claim 4 wherein said source of compressed gas comprises compressor means.

\* \* \* \* \*